United States Patent
Kerc

(12) 
(10) Patent No.: US 6,680,341 B1
(45) Date of Patent: Jan. 20, 2004

(54) STABLE PHARMACEUTICAL FORMULATION COMPRISING A HMG-COA REDUCTASE INHIBITOR

(75) Inventor: Janez Kerc, Ljubljana (SI)

(73) Assignee: LEK Pharmaceuticals d.d., Ljubljana (SI)

( * ) Notice: Subject to any disclaimer, the term of this patent is extended or adjusted under 35 U.S.C. 154(b) by 0 days.

(21) Appl. No.: 09/600,436

(22) PCT Filed: Oct. 29, 1999

(86) PCT No.: PCT/IB99/01749
§ 371 (c)(1), (2), (4) Date: Oct. 16, 2000

(87) PCT Pub. No.: WO00/35425
PCT Pub. Date: Jun. 22, 2000

(30) Foreign Application Priority Data

Dec. 16, 1998 (SI) .............................. P-9800309

(51) Int. Cl.$^7$ ...................... A61K 31/225; A61K 31/40
(52) U.S. Cl. ...................... 514/547; 514/429; 514/423
(58) Field of Search ................... 514/547, 429, 514/423

(56) References Cited

U.S. PATENT DOCUMENTS 5,798,375 A * 8/1998 Tsujita et al. ............... 514/369

FOREIGN PATENT DOCUMENTS

| EP | 0 336 298 B1 | 10/1989 |
| EP | 0 336 298 A1 | 10/1989 |
| EP | 000547000 A1 * | 12/1992 |
| EP | 0 547 000 A1 | 6/1993 |
| WO | WO 94/16693 | 8/1994 |
| WO | WO 97/23200 * | 7/1997 |

OTHER PUBLICATIONS

The Physicians Desk Reference, electronic version, http://www.pdrel.com/pdr/static.htm?path=controlled/searchpdrindex.htm.*
Novartis Pharmaceuticals Canada Inc. Prescribing Information Lescol (fluvastatin sodium) see p. 21).*
Hungarian Search Report from Application HU P0104258/8.

* cited by examiner

Primary Examiner—Phyllis G. Spivack
Assistant Examiner—Donna Jagoe
(74) Attorney, Agent, or Firm—Bromberg & Sunstein LLP

(57) ABSTRACT

Atorvastatin and pravastatin may be destabilized by the environmental factors, their degradation may also be accelerated by interactions with other pharmaceutical ingredients, such as fillers, binders, lubricants, glidants and disintegrating agents, therefore the pharmaceutical ingredients and the process for preparation of the pharmaceutical formulation should be meticulously chosen to avoid the aforementioned undesired interactions and reactions.

The present invention relates to a stable solid pharmaceutical formulation for the treatment of hypercholesterolemia and hyperlipidemia. More precisely, the present invention relates to the new stable solid pharmaceutical formulation containing as an active ingredient, an HMG-CoA reductase inhibitor, such as atorvastatin and pravastatin and pharmaceutically acceptable salts thereof.

39 Claims, 4 Drawing Sheets

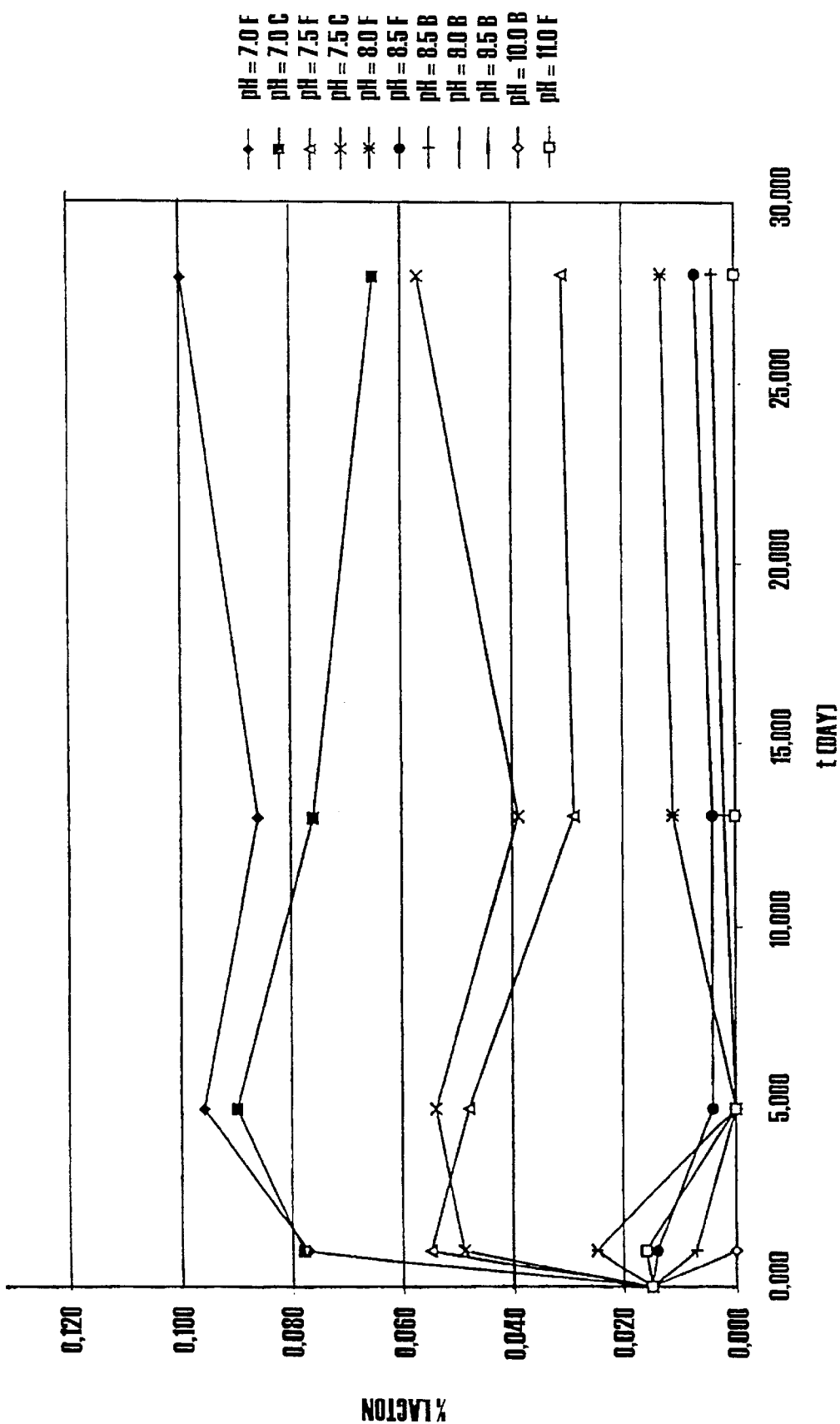

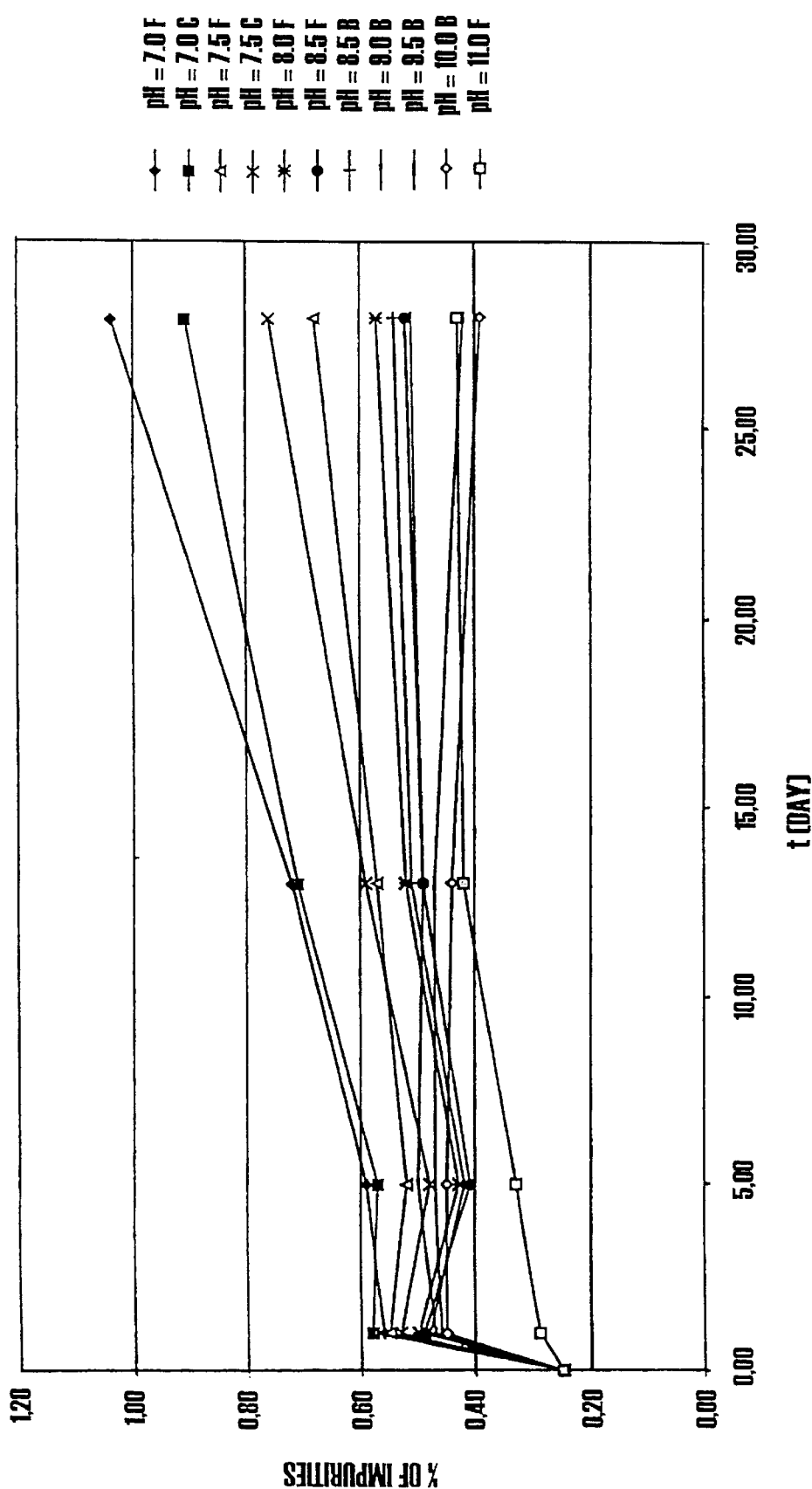

US 6,680,341 B1

STABLE PHARMACEUTICAL FORMULATION COMPRISING A HMG-COA REDUCTASE INHIBITOR

FIELD OF THE INVENTION

The present invention relates to a new stable solid pharmaceutical formulation which is particularly suitable for the treatment of hypercholesterolemia and hyperlipidemia. More precisely, the present invention relates to the new stable solid pharmaceutical formulation containing as an active substance a HMG-CoA reductase inhibitor, such as atorvastatin, pravastatin, fluvastatin and cervastatin, or pharmaceutically active salts thereof.

BACKGROUND OF THE INVENTION

Lovastatin, pravastatin, simvastatin, mevastatin, atorvastatin, fluvastatin and cervastatin, derivatives and analogs thereof are known as HMG-CoA reductase inhibitors and are used as antihypercholesterolemic agents. The majority of them are produced by fermentation using microorganisms of different species identified as species belonging to Aspergillus, Monascus, Nocardia, Amycolatopsis, Mucor or Penicillium genus. Some are obtained by treating the fermentation products using the methods of chemical synthesis like simvastatin or they are the products of total chemical synthesis like fluvastatin, atorvastatin and cervastatin.

The purity of the active substance is an important factor for manufacturing a safe and effective pharmaceutical formulation. Maximum possible purity of the product is of particular importance if the pharmaceutical product must be taken on a longer term basis in the treatment or prevention of high cholesterol levels in blood. Accumulation of impurities from drugs of a lower level of purity may cause a variety of side effects during treatment. Besides impurities, that cannot be completely eliminated in the process of preparation of the active substance, degradation products occurring by subjecting the final pharmaceutical formulation to various environmental factors such as temperature, moisture, low pH and light, may also impose a problem. HMG-CoA reductase inhibitors occurring in the form of salts in the final pharmaceutical formulation, such as atorvastatin, pravastatin, fluvastatin and cervastatin, are particularly sensitive to an acidic environment in which hydroxy acids are degraded into a lactone.

Apart from the fact that the aforementioned active substance may be destabilised by the environmental factors, their degradation may also be accelerated by interactions with other pharmaceutical ingredients, such as fillers, binders, lubricants, glidants and disintegrating agents. Therefore, the pharmaceutical ingredients and the process for preparation of the pharmaceutical formulation should be meticulously chosen to avoid the aforementioned undesired interactions and reactions.

The stability of the active substance in an acidic environment is one of the major problems in the case of statins in the form of salts. One of possible solutions of the aforementioned problem is described in EP 0 336 298, disclosing a stable pharmaceutical formulation for pravastatin. The essence of the formulation is to maintain an alkaline environment so that the aqueous dispersion of the pharmaceutical formulation reaches a pH above 9, preferably about 10. In addition to the active substance pravastatin, the composition of the invention includes a basifying agent, such as magnesium oxide which imparts a pH to an aqueous dispersion of the aforementioned formulation above 9. In view of the stability of the active substance such a formulation is effective. However, the local alkaline environment occurring at the site of dissolution of the pharmaceutical formulation may have a negative impact on the gastric mucosa with its normally acidic environment. This negative impact may be particularly evident for patients with a damaged gastric mucous membrane where the mucosa per se is not able to create a sufficient acidic environment inside the stomach for normal digestive functioning. It is particularly important in chronic therapies as in the case of prophylaxis or treatment with HMG-CoA reductase inhibitors.

SUMMARY OF THE INVENTION

It is an object of the present invention to provide a pharmaceutical formulation containing as an active substance a HMG-CoA reductase inhibitor which exerts an excellent stability while avoiding the afore mentioned disadvantages. It is a particular object to provide a stabilized active substance as such where the HMG-CoA reductase inhibitor is precautionary protected from being degraded.

It is a further object to provide a process for the preparation of a stable pharmaceutical formulation which exerts an excellent stability while avoiding the afore mentioned disadvantages.

These and further objects are accomplished by the present invention.

According to the present invention, there is provided a stable solid pharmaceutical formulation containing as an active substance a HMG-CoA reductase inhibitor, wherein an active substance is contained which is capable of providing a pH in the range from 7 to 11. Within the meaning of the present invention, the term "active substance" denotes a HMG-CoA reductase inhibitor alone or a mixture thereof with a small amount of a buffering agent. Therefore, the present invention also makes available a stabilized pharmaceutically active substance as such, which active substance consists of a HMG-CoA reductase inhibitor and a low amount of a buffering agent.

According to the present invention, there is further provided a stable solid pharmaceutical formulation containing as an active substance a HMG-CoA reductase inhibitor, wherein the pharmaceutical formulation is capable of providing a pH below 9.

In addition, according to the present invention, there is provided suitable processes for the preparation of the above specified stable solid pharmaceutical formulation.

According to the present invention, there is further provided a method for the stabilization of a HMG-CoA reductase inhibitor as an active substance in a solid pharmaceutical formulation, wherein an HMG-CoA reductase inhibitor being capable of providing a pH in the range from 7 to 11 is incorporated into a pharmaceutical formulation which is capable of providing a pH below 9.

BRIEF DESCRIPTION OF THE DRAWINGS

FIG. 2 is a diagram which shows the occurrence of pravastatin in lactone form when pravastatin was dissolved in different buffers with the pH in a range between 7 and 11 (F=phosphate, C=citrate, B=borate).

FIG. 3 is a diagram which shows the formation of different degradation products (impurities) when pravastatin was dissolved in different buffers with the pH in a range between 7 and 11 (F=phosphate, C=citrate, B=borate).

DETAILED DESCRIPTION OF THE PREFERRED EMBODIMENTS

In the inventor's investigations, it was found that there are three major reasons for instability problems in case of a pharmaceutical formulation containing an active substance and in case of a bulk active substance.

Figure 1:
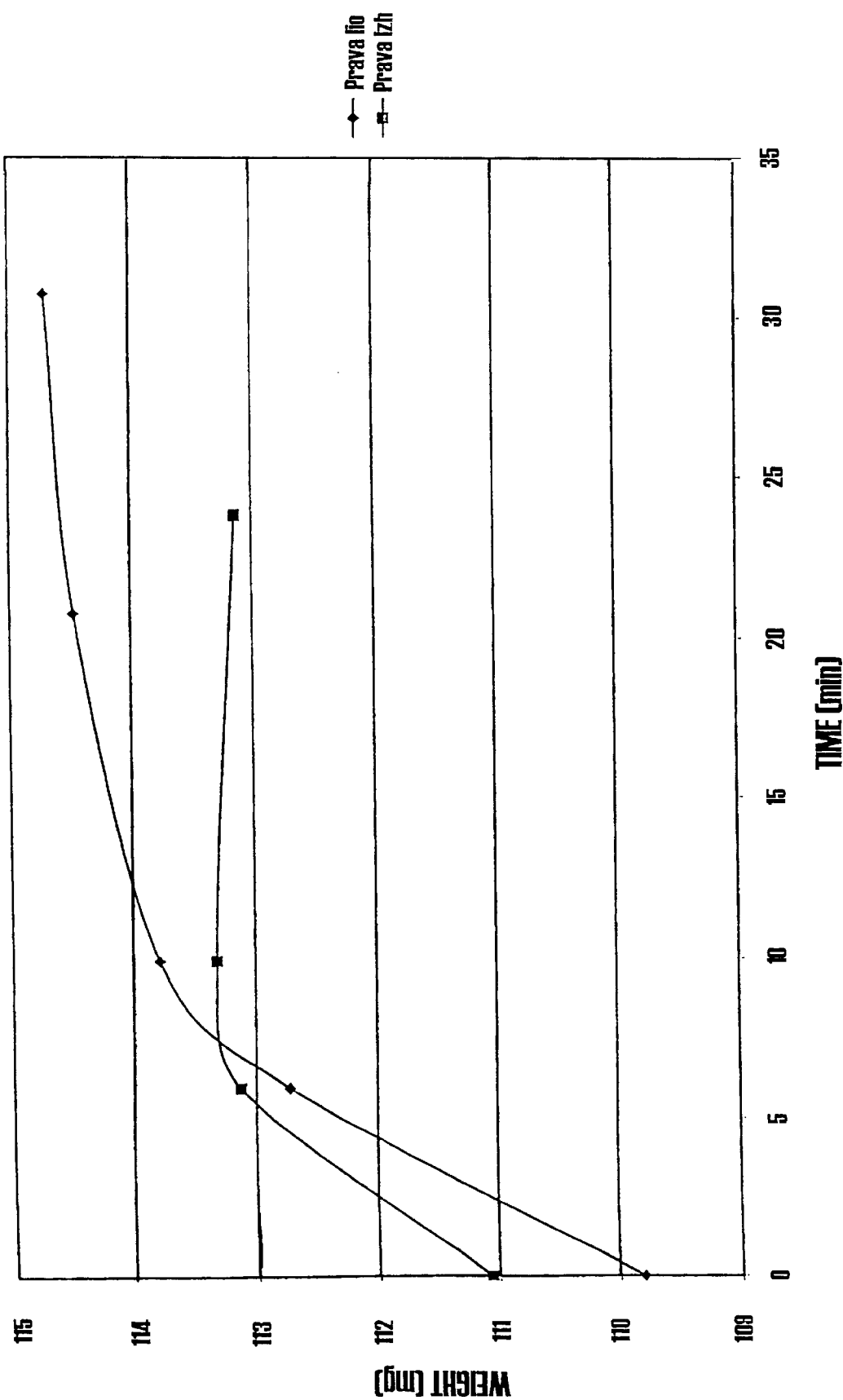
FIG. 1a is a diagram which shows the growth of weight of a sample of pravastatin in crystal form and a sample of lyophilised pravastatin when exposed to air moisture.
FIG. 1b shows the corresponding difference in the starting weight and the weight in time.
Figure 1B:
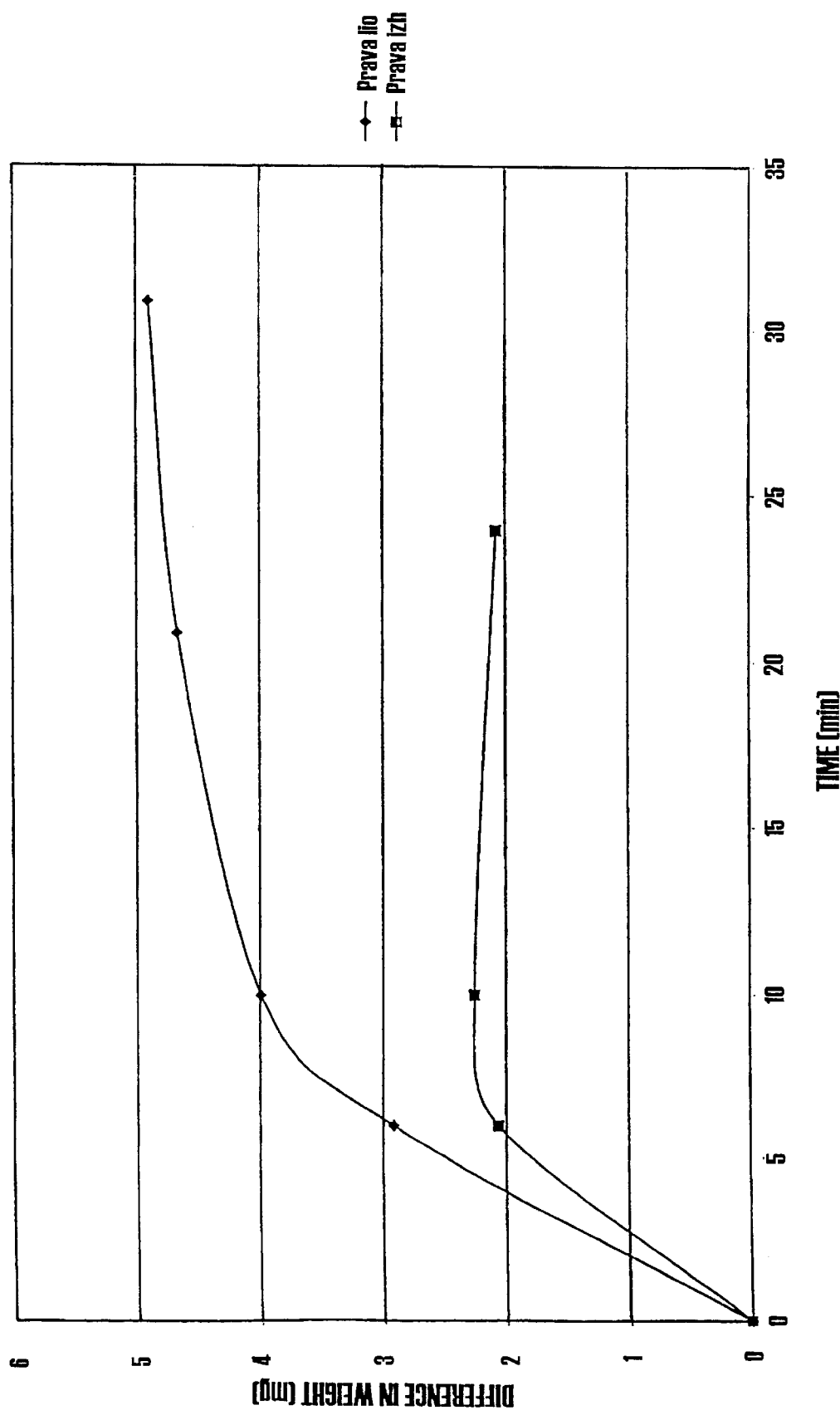

First, the active substance as such is very hygroscopic and it is impossible to remove all water from it. This is illustrated by the following experiment: 111.07 mg of pravastatin in crystal form (prava izh) and 109.8 mg of lyophilized pravastatin (prava lio) were exposed to air moisture. Their weights were measured in different time intervals. The growth of weight of both samples and the difference in the starting weight and the weight in time are illustrated in FIGS. 1a and 1b.

Another observation was that carbon dioxide from the air can irreversibly bind to the active substance and can cause a drop of pH. This is illustrated by the following experiment: 5 g of pravastatin sodium were dissolved in 30 ml of methanol, the pH was adjusted to 10 with 3% aqueous solution of NaOH. 400 ml of ethylacetate were added and the crystals of pravastatin sodium were formed. Crystals were filtered and dried and then put into three different atmospheres: normal air, nitrogen atmosphere and carbon dioxide atmosphere. In normal air and in the nitrogen atmosphere the pH remained the same during a period of 24 hours (normal air: 9.2, nitrogen: 9.5), but in the carbon dioxide atmosphere the pH dropped in the first two minutes from 9.2 to 6.9. After 12 minutes the pH was 6.6 and after 1 hour the pH was 6.5. After that, the pH remained constant. The third observation is that a sufficient stabilization of the active substance is already obtained at a pH of at least 7.0, but a beneficially high stability is effected at a pH of at least 8.0. We have noticed that at a pH below 8 the formation of lactone has occured and also the amount of other impurities has increased. The presence of humidity in the air and a carbon dioxide-rich atmosphere makes the negative effect of a low pH even stronger. This is illustrated by the following experiment: Pravastatin was dissolved in different buffers with the pH in a range between 7 and 11 (F=phosphate, C=citrate, B=borate). The occurrence of pravastatin in lactone form and the formation of different degradation products (impurities) was measured after 1, 5, 13 and 28 days. The results are shown in FIGS. 2 and 3.

In the present invention, we have surprisingly found that a sufficient stability of the active substance, which is a HMG-CoA reductase inhibitor preferably in the form of salt, can be also obtained by using a pharmaceutical formulation which does not create a marked alkaline environment in an aqueous dispersion.

Further, we have found that for the stability and digestibility of a pharmaceutical formulation both the pH generated by the formulation in an aqueous medium (usually being a dispersion) and the pH of the active substance (HMG-CoA reductase inhibitor) are of great importance.

Another surprising finding was that a sufficient stability of a HMG-CoA reductase inhibitor in the form of a salt in bulk can be obtained by the addition of small amounts of a buffering agent to the pure HMG-CoA reductase inhibitor in the form of salt. Such an addition of small amounts of buffering agents avoids the negative effect of water already present in the bulk substance and of moisture from the air, to avoid the negative effect of low pH caused by other ingredients which will be co-admixed to the pharmaceutical formulation, and to avoid the possible lowering of the pH caused by carbon dioxide.

The active substance and the pharmaceutical formulation according to the present invention were designed to avoid the negative effect of the water present in the bulk substance and in the pharmaceutical formulation, to avoid the negative effect of low pH which can be caused by other ingredients of the pharmaceutical formulation and to avoid possible lowering of the pH caused by carbon dioxide.

The most acceptable stability of the active substance in the formulations is obtained with an active substance which is capable of providing a pH in the range from 7 to 11. The pH value is the one which is obtained when the pH of an aqueous medium containing said active substance would be measured. In the stable pharmaceutical formulation according to the present invention, the basic pH of the active substance has a minimal influence on the pH of the formulation which is lower than 9. By creating locally an environment around the active substance which affords the best stability for the active substance, the potential of negative impact of other ingredients of the composition of the pharmaceutical formulation is reduced, and possible reactions among the active substance and the rest of the ingredients of the composition of the pharmaceutical formulation are also less favoured. Accordingly, the active substance is maintained in a stable form when an active substance which is capable of providing a pH in an aqueous medium in the range from 7 to 11 is added to the pharmaceutical formulation.

The active substance being added to the formulation of the present invention generally is a HMG-CoA reductase inhibitor in the form of a salt. The pH of the active substance may be adjusted within the above specified range in the course of preparing the salt of the HMG-CoA reductase inhibitor from the acid form and an alkaline substance. As an example, the preparation of pravastatin sodium from pravastatin acid and sodium hydroxide may be mentioned. For a preferred adjustment of the pH of the active substance to be incorporated into the formulation within the above specified range of 7 to 11, the active substance is further mixed with an appropriate buffering agent. Accordingly, the active substance may contain small amounts of a buffering agent, preferably less than 1%, more preferably 0.1 to 0.5%, most preferably approximately 0.3%, based on the weight of the active substance added to the formulation. A suitable buffering agent for this purpose is carbonate buffer or phosphate buffer, such as sodium carbonate of sodium phosphate. For example, an amount 0.3% of sodium carbonate in pravastatin results in a pH of pravastatin between 9 and 10. Thus, it is possible to mix pravastatin with other ingredients of the pharmaceutical formulation without fear that a degradation can be caused by the contact of pravastatin with acidic ingredients as a microenvironment of pravastatin is still basic due to the addition of small amounts of a buffering agent. This addition of small amounts of a buffering agent is also important for an easier handling of the pravastatin bulk without special requirements for a carbon dioxide free atmosphere. Preferably, the acidifying effect of carbon dioxide on the final formulation is neutralised by further addition of an appropriate buffering agent to adjust the pH of the formulation in the above specified range, preferably by addition of 20%, more preferably of 10% per weight based on the total weight of the tablet. Any buffering agent capable of adjusting the pH of the total formulation in the desired range is suitable, including sodium or potassium citrate, sodium phosphate, dibasic sodium phosphate, calcium carbonate, hydrogen phosphate, phosphate, sulphate, sodium or magnesium carbonate, sodium ascorbinate, benzoate, sodium or potassium hydrogen carbonate, lauryl sulphate, or mixtures of such buffering agents. Citrate buffer, carbonate buffer and phosphate or hydrogen phosphate buffer may be mentioned as specific examples.

Preferably, an active substance contained in the pharmaceutical formulation according to the present invention is capable of providing a pH in the range from 8 to 10.

Furthermore, the active substance may be selected from the group consisting of pravastatin, atorvastatin, fluvastatin, cerivastatin and a pharmaceutically acceptable salt thereof. Preferably, the active substance is a sodium salt of pravastatin (pravastatin Na) or a calcium salt of atorvastatin (atorvastatin Ca).

As mentioned above, it is a further significant aspect of the present invention that the pharmaceutical formulation is capable of providing a pH below 9, preferably below 8.5. The lower limit of the pH generated by the pharmaceutical formulation suitably is 6, preferably 7.

By following the concepts of the present invention, the solid pharmaceutical formulation is stable such that the HMG-CoA reductase inhibitor as the active substance does not tend to be decomposed and essentially retains its activity. Thereby, it is ensured that the active substance in the pharmaceutical formulation according to the present invention shows a sufficient stability while, at the same time, avoiding the negative impact of a high local alkaline environment at the site of dissolution of the pharmaceutical formulation on the gastric mucosa which would occur if the pH of an aqueous dispersion of the pharmaceutical formulation is 9 or more and which results in anormal digestive functioning.

The pharmaceutical formulation of this invention may include, in addition to the HMG-CoA reductase inhibitor which is sensitive to a low pH environment, one or more fillers, such as microcrystalline cellulose, lactose, sugars, starches, modified starch, mannitol, sorbitol and other polyols, dextrin, dextran and maltodextrin, calcium carbonate, calcium phosphate and/or hydrogen phosphate, sulphate, one or more binders, such as lactose, starches, modified starch, dextrin, dextran and maltodextrin, microcrystalline cellulose, sugars, polyethylene glycols, hydroxypropyl cellulose, hydroxypropyl methylcellulose, ethylcellulose, hydroxyethyl cellulose, methylcellulose, carboxymethyl cellulose, gelatin, acacia gum, tragacanth, polyvinylpyrrolidone, magnesium aluminium silicate, one or more disintegrating agents such as croscarmellose sodium, cross-linked polyvinylpyrrolidone, cross-linked carboxymethyl starch, starches and microcrystalline cellulose, magnesium aluminium silicate, polyacrylin potassium, one or more different glidants such as magnesium stearate, calcium stearate, zinc stearate, calcium behenate, sodium stearyl fumarate, talc, magnesium trisilicate, stearic acid, palmitic acid, carnauba wax, silicon dioxide, one or more buffering agents such as sodium or potassium citrate, sodium phosphate, dibasic sodium phosphate, calcium carbonate, hydrogen phosphate, phosphate, sulphate, sodium or magnesium carbonate, sodium ascorbinate, benzoate, sodium or potassium hydrogen carbonate, lauryl sulphate, or mixtures of such buffering agents.

If required any, the formulation may also include surfactants and other conventional components for solid, pharmaceutical formulations such as colouring agents, lakes, aromas and adsorbents. As surfactants the following may be used: ionic surfactants, such as sodium lauryl sulphate or non-ionic surfactants such as different poloxamers (polyoxyethylene and polyoxypropylene copolymers), natural or synthesized lecithins, esters of sorbitan and fatty acids (such as Span®, manufactured by Atlas Chemie), esters of polyoxyethylenesorbitan and fatty acids (such as Tween®, manufactured by Atlas Chemie), polyoxyethylated hydrogenated castor oil (such as Cremophor®, manufactured by BASF), polyoxyethylene stearates (such as Brij®, manufactured by Atlas Chemie), dimethylpolysiloxane or any combination of the above mentioned surfactants.

If the solid pharmaceutical formulation is in the form of coated tablets, the coating may be prepared from at least one film-former such as hydroxypropyl methylcellulose, hydroxypropyl cellulose, at least from one plasticizer such as polyethylene glycols, dibutyl sebacate, triethyl citrate, and other pharmaceutical auxiliary substances conventional for film coatings, such as pigments, fillers and others.

The solid pharmaceutical formulations according to the present invention may be prepared as described below:

The mixture of the active substance, filler, binder, buffering agent, disintegrating agent and if required a surfactant and other conventional ingredients for solid pharmaceutical formulations is homogenised employing suitable mixers. Glidants and/or lubricants are added and the mixture is re-homogenised. The resulting mixture is compressed into tablets or filled into capsules. If needed, tablets can be film-coated.

The mixture of the active substance, filler, binder, buffering agent, disintegrating agent and if required a surfactant and other conventional ingredients for solid pharmaceutical formulations is homogenised employing suitable mixers, granulated with a suitable solvent such as water, ethanol, methanol, isopropyl alcohol, n-butyl alcohol, acetone, diethyl ether, ethyl acetate, isopropyl acetate, methyl acetate, dichloromethane and methanol, and mixtures of these solvents such as ethanol and acetone, methanol and acetone, dichloromethane and methanol, and the mixtures thereof. The resulting granulation is dried in suitable dryers such as standard plate dryers, fluid bed dryers, vacuum and microwave dryers. To the dried granulation, glidants and/or lubricants and if required other conventional ingredients for solid pharmaceutical formulations are added. The resulting mixture is rehomogenised and compressed into tablets or filled into capsules. Optionally, tablets are film-coated.

Moreover, according to the present invention the HMG-CoA reductase inhibitor as an active substance in a solid pharmaceutical formulation can be effectively stabilized by incorporating a HMG-CoA reductase inhibitor, which is capable of providing a pH in the range from 7 to 11, into a pharmaceutical formulation which is capable of providing a pH below 9. The pH generated by the pharmaceutical formulation may be adjusted by the incorporation of appropriate agents such as buffering agents and the like.

The present invention is illustrated but by no means limited by the following examples.

EXAMPLES

Example 1

The pharmaceutical formulation with the active ingredient pravastatin sodium in the form of tablets was prepared as follows: the hereinunder listed ingredients were homogenised and the resulting mixture was then compressed into tablets each containing 5, 10, 20 or 40 mg of pravastatin sodium.

The pH of the aqueous dispersion of this formulation is 8.3.

| Ingredients | % by weight |
|---|---|
| Pravastatin sodium (pH 8.2) | 5% |
| Lactose | 37.5% |
| Microcrystalline cellulose | 38% |
| Sodium citrate | 10% |
| Magnesium aluminium silicate | 2% |
| Polyacrylin potassium | 3% |
| Talc | 3% |
| Silicon dioxide | 0.5% |
| Magnesium stearate | 1% |

Example 2

The pharmaceutical formulation with the active ingredient pravastatin sodium in the form of tablets was prepared as follows: the hereinunder listed ingredients were homogenised and the resulting mixture was then compressed into tablets each containing 5, 10, 20, 40 or 80 mg of pravastatin sodium.

The pH of the aqueous dispersion of this formulation is 8.0.

| Ingredients | % by weight |
|---|---|
| Pravastatin sodium (pH 8.5) | 10% |
| Lactose | 32% |
| Microcrystalline cellulose | 37% |
| Sodium citrate | 10% |
| Croscarmellose sodium | 2% |
| Sodium lauryl sulphate | 0.5% |
| Polyacrylin potassium | 3% |
| Talc | 3% |
| Silicon dioxide | 0.5% |
| Calcium stearate | 2% |

Example 3

The pharmaceutical formulation with the active ingredient pravastatin sodium in the form of tablets was prepared as follows: the first six hereinunder listed ingredients were homogenised, granulated with water, dried, the remainder of the below listed ingredients were added and homogenised and the resulting mixture was then compressed into the tablets each containing 5, 10, 20 or 40 mg of pravastatin sodium.

The pH of the aqueous dispersion of this formulation is 8.2.

| Ingredients | % by weight |
|---|---|
| Pravastatin sodium (pH 9) | 5% |
| Lactose | 20% |
| Microcrystalline cellulose | 20% |
| Hydroxypropyl cellulose | 1.5% |
| Sodium citrate | 10% |
| Magnesium aluminium silicate | 2% |
| Polyacrylin potassium | 3% |
| Microcrystalline cellulose | 35% |
| Talc | 3% |
| Magnesium stearate | 0.5% |

Example 4

The pharmaceutical formulation with the active ingredient pravastatin sodium in the form of tablets was prepared as follows (ingredients are listed in the following table): the mixture of the active substance, filler, buffering agent, disintegrant and surfactant is homogenised employing suitable mixers. Glidants and lubricants are added and the mixture is re-homogenised. The resulting mixture is compressed into tablets. The pH of the aqueous dispersion of this formulation is 8.5.

| Ingredient | % by weight | function |
|---|---|---|
| pravastatin Sodium* | 8.3 | active substance |
| lactose | 58.3 | filler |
| microcrystalline cellulose | 14.4 | filler |
| $Na_2HPO_4$ | 10 | buffering agent |
| Na lauryl sulphate | 0.4 | absorption accelerator, surfactant |
| cross-linked carboxymethylcellulose | 4 | disintegrant |
| colloidal silicon dioxide | 0.5 | glidant |
| talc | 3 | glidant, lubricant |
| magnesium stearate | 1 | lubricant |

*pravastatin contains 0.3% of $Na_2CO_3$, so that the pH of the active substance is between 9 and 10. The percentage in the above mentioned formulation is calculated for the tablets containing 40 mg of pravastatin. The amount of pravastatin can be 80, 40, 20, 10 or 5 mg.

Example 5

The pharmaceutical formulation with the active ingredient pravastatin sodium in the form of tablets was prepared as in Example 4. The resulting mixture is compressed into tablets. The pH of the aqueous dispersion of this formulation is 8.3.

| Ingredient | % by weight | function |
|---|---|---|
| pravastatin sodium* | 8.3 | active substance |
| lactose | 58.3 | filler |
| microcrystalline cellulose | 16.5 | filler |
| $Na_2HPO_4$ (dried) | 7.9 | buffering agent |
| sodium lauryl sulphate | 0.4 | absorption accelerator, surfactant |
| cross-linked carboxymethylcellulose | 4 | disintegrant |
| colloidal silicon dioxide | 0.5 | glidant |
| talc | 3 | glidant, lubricant |
| magnesium stearate | 1 | lubricant |

*pravastatin contains 0.3% of $Na_2CO_3$, so that the pH of the active substance is between 9 and 10. The amount of pravastatin can be 80, 40, 20, 10 or 5 mg.

Example 6

The pharmaceutical formulation with the active ingredient atorvastatin calcium in the form of tablets was prepared as in Example 4. The resulting mixture is compressed into tablets.

| Ingredient | weight (mg) | function |
|---|---|---|
| Atorvastatin calcium | 20.0 | active substance |
| lactose | 140.0 | filler |
| microcrystalline cellulose | 34.8 | filler |

-continued

| Ingredient | weight (mg) | function |
|---|---|---|
| Na$_2$HPO$_4$ (dried) | 24.0 | buffering agent |
| Na lauryl sulphate | 2.0 | absorption accelerator, surfactant |
| cross-linked carboxymethylcellulose | 9.6 | disintegrant |
| colloidal silicon dioxide | 1.2 | glidant |
| talc | 7.2 | glidant, lubricant |
| magnesium stearate | 1.2 | lubricant |

In case of higher or lower dosages of atorvastatin calcium (80, 40, 10 or 5 mg), proportional higher or smaller amounts of other ingredients are used, or proportional bigger or smaller tablets are prepared.

Tablets containing pravastatin or atorvastatin which were formed according to examples 1 to 6 were subjected to stability studies and it was found that the tablets provide an excellent stability; essentially no degradation products of pravastatin or atorvastatin were observed.

What is claimed is:

1. A stabilized pharmaceutical formulation containing as an active ingredient an HMG-CoA reductase inhibitor, wherein said HMG-CoA reductase inhibitor is selected from the group consisting of pravastatin and atorvastatin and a pharmaceutically acceptable salt thereof, and wherein the formulation includes an active composition consisting of said active ingredient and a buffering agent, wherein the active composition has a pH in the range from 7 to 11;

at least one constituent selected from the group consisting of a filler, a binder, a disintegrating agent and a glidant; and additional buffering agent, wherein the pharmaceutical formulation has a pH below 9.

2. A stable solid pharmaceutical formulation according to claim 1, wherein the pharmaceutical formulation has a pH from 6 to less than 9.

3. A stable solid pharmaceutical formulation according to claim 1, wherein the pharmaceutical formulation has a pH in the range from 7 to 8.5.

4. A stable solid pharmaceutical formulation according to claim 1, wherein said active substance has a pH in the range from 8 to 10.

5. A stable solid pharmaceutical formulation as defined in claim 1, wherein said active ingredient is an HMG-CoA reductase inhibitor in the form of a salt.

6. A stable solid pharmaceutical formulation according to claim 1, wherein said incorporated active ingredient contains a buffering agent in an amount of less than 0.75% by weight based on the total weight of the active substance.

7. A stable solid pharmaceutical formulation as defined in claim 1, wherein said active ingredient is a sodium salt of pravastatin or a calcium salt of atorvastatin.

8. A stable solid pharmaceutical formulation as defined in claim 1, which further comprises at least one constituent selected from the group consisting of coloring agents, lakes, aromas, adsorbents, film formers and plasticizers.

9. A stabilized pharmaceutically active substance consisting only of a mixture of an HMG-CoA reductase inhibitor and a buffering agent imparting a pH in the local environment around the active substance in the range from 7 to 11, wherein said HMG-CoA reductase inhibitor is selected from the group consisting pravastatin and atorvastatin and a pharmaceutically acceptable salt thereof and wherein said buffering agent is present in an amount of less than 1% by weight based on the total weight of the pharmaceutically active substance.

10. A stabilized pharmaceutically active substance according to claim 9, wherein said HMG-CoA reductase inhibitor is in the form of a salt.

11. A stabilized pharmaceutically active substance according to claim 9, wherein said buffering agent imparts a pH in the range from 7 to 11 to the pharmaceutically active substance.

12. A stabilized pharmaceutically active substance according to claim 9, wherein said HMG-CoA reductase inhibitor is a sodium salt of pravastatin or a calcium salt of atorvastatin.

13. A stabilized pharmaceutically active substance according to claim 9, wherein said buffering agent is present in an amount of less than 0.75% by weight based on the total weight of the pharmaceutically active substance.

14. A stable solid pharmaceutical formulation containing as an active substance a salt of an HMG-CoA reductase inhibitor, wherein said HMG-CoA reductase inhibitor is selected from the group consisting of pravastatin and atorvastatin and wherein said active substance has a pH in the range from 7 to 11 and is obtained in the course of preparing the salt of the HMG-CoA reductase inhibitor from a free acid form of said inhibitor and an alkaline substance.

15. A stable solid pharmaceutical formulation according to claim 14, wherein said active substance has a pH in the range from 8 to 10.

16. A stable solid pharmaceutical formulation according to claim 14, wherein said active substance contains a buffering agent in an amount of less than 0.75% by weight based on the total weight percent of the active substance.

17. A stable solid pharmaceutical formulation according to claim 14, wherein said salt of an HMG-CoA reductase inhibitor is a sodium salt of pravastatin or a calcium salt of atorvastatin.

18. A stable solid pharmaceutical formulation according to claim 14, which further comprises at least one constituent selected from the group consisting of a filler, a binder, a disintegrating agent, a glidants, a buffering agent; optionally further comprising at least one constituent selected from among coloring agents, lakes, aromas, adsorbents, film formers, and plasticizers.

19. A stabilized pharmaceutical formulation containing as an active ingredient an HMG-CoA reductase inhibitor, wherein said HMG-CoA reductase inhibitor is selected from the group consisting of pravastatin and atorvastatin and a pharmaceutically acceptable salt thereof, and wherein the formulation includes an active composition consisting of said active ingredient and an alkaline substance, wherein the active composition has a pH in the range from 7 to 11, and at least one constituent selected from the group consisting of a filler, a binder, a disintegrating agent and a glidant, wherein the pharmaceutical formulation has a pH below 9.

20. A stable solid pharmaceutical formulation according to claim 19, wherein the pharmaceutical formulation has a pH from 6 to less than 9.

21. A stable solid pharmaceutical formulation according to claim 19, wherein the pharmaceutical formulation has a pH in the range from 7 to 8.5.

22. A stable solid pharmaceutical formulation according to claim 19, wherein said active substance has a pH in the range from 8 to 10.

23. A stable solid pharmaceutical formulation according to claim 19, wherein said active composition further contains a buffering agent in an amount of less than 0.75% by weight based on the total weight of the active substance.

24. A stable solid pharmaceutical formulation according to claim 19, wherein additional amounts of a buffering agent are incorporated into said pharmaceutical formulation.

25. A stable solid pharmaceutical formulation according to claim 19, wherein said active ingredient is a sodium salt of pravastatin or a calcium salt of atorvastatin.

26. A stable solid pharmaceutical formulation according to claim 19, which further comprises at least one constituent selected from the group consisting of coloring agents, lakes, aromas, adsorbents, film formers and plasticizers.

27. A stabilized pharmaceutically active substance consisting of a salt of an HMG-CoA reductase inhibitor, wherein said HMG-CoA reductase inhibitor is selected from the group consisting of pravastatin and atorvastatin and wherein said active substance has a pH in the range from 7 to 11 and is obtained in the course of preparing the salt of the HMG-CoA reductase inhibitor from an acid form of said inhibitor and an alkaline substance.

28. A stabilized pharmaceutically active substance according to claim 23, wherein said active substance is a sodium salt of pravastatin or a calcium salt of atorvastatin.

29. A stabilized pharmaceutically active substance consisting of a salt of an HMG-CoA reductase inhibitor, wherein said HMG-CoA reductase inhibitor is selected from the group consisting of pravastatin and atorvastatin and wherein said active substance has a pH in the range from 7 to 11 and is obtained in the course of preparing the salt of the HMG-CoA reductase inhibitor from an acid form of said inhibitor and an alkaline substance, and further contains a buffering agent, wherein said buffering agent is present in an amount of less than 0.75% by weight based on the total weight of the pharmaceutically active substance.

30. A stabilized pharmaceutically active substance consisting of a salt of an HMG-CoA reductase inhibitor, wherein said HMG-CoA reductase inhibitor is selected from the group consisting of pravastatin and atorvastatin and wherein said active substance has a pH in the range from 7 to 11 and is obtained in the course of preparing the salt of the HMG-CoA reductase inhibitor from an acid form of said inhibitor and an alkaline substance, and further contains a buffering agent, wherein said buffering agent is present in an amount of less than 0.5% by weight based on the total weight of the pharmaceutically active substance.

31. A stabilized pharmaceutically active substance consisting of a salt of an HMG-CoA reductase inhibitor, wherein said HMG-CoA reductase inhibitor is selected from the group consisting of pravastatin and atorvastatin and wherein said active substance has a pH in the range from 7 to 11 and is obtained in the course of preparing the salt of the HMG-CoA reductase inhibitor from an acid form of said inhibitor and an alkaline substance, and further contains a buffering agent, wherein said buffering agent is present in an amount from 0.1 to 0.5% by weight based on the total weight of the pharmaceutically active stance.

32. A stabilized pharmaceutical formulation containing as an active ingredient an HMG-CoA reductase inhibitor, wherein said HMG-CoA reductase inhibitor is selected from the group consisting of pravastatin and atorvastatin and a pharmaceutically acceptable salt thereof, and wherein the formulation includes an active composition consisting of said active ingredient and a first buffering agent, wherein the active composition has a pH in the range from 7 to 11, and a second buffering agent, wherein the pharmaceutical formulation has a pH, below 9.

33. A stable pharmaceutical formulation according to claim 32, which further comprises at least one constituent selected from the, group consisting of a filler, a binder, a disintegrating agent, a glidant; and optionally at least one constituent selected from among coloring agents, lakes, aromas, adsorbent, film formers, and plasticizers.

34. A stable pharmaceutical formulation according to claim 32, wherein the pharmaceutical formulation has a pH from 6 to less than 9.

35. A stable pharmaceutical formulation according to claim 32, wherein the pharmaceutical formulation has a pH in the range from 7 to 8.5.

36. A stable pharmaceutical formulation according to claim 32, wherein the active composition has a pH in the range from 8 to 10.

37. A stable pharmaceutical formulation according to claim 32, wherein the active ingredient is an HMG-CoA reductase inhibitor in the form of a salt.

38. A stable pharmaceutical formulation according to claim 32, wherein the active composition contains the first buffering agent in an amount of less than 0.75% by weight based on the total weight of the active composition.

39. A stable pharmaceutical formulation according to claim 32, wherein the active ingredient is a sodium salt of pravastatin (pravastatin Na) or a calcium salt of atorvastatin (atorvastatin Ca).

\* \* \* \* \*

UNITED STATES PATENT AND TRADEMARK OFFICE
CERTIFICATE OF CORRECTION

PATENT NO. : 6,680,341 B1
DATED : January 20, 2004
INVENTOR(S) : Janez Kerc

It is certified that error appears in the above-identified patent and that said Letters Patent is hereby corrected as shown below:

<u>Column 11,</u>
Line 22, replace "claim 23" with -- claim 27 --.

Signed and Sealed this

Thirty-first Day of August, 2004

JON W. DUDAS
*Director of the United States Patent and Trademark Office*